(12) United States Patent
Hardin et al.

(10) Patent No.: US 7,798,331 B2
(45) Date of Patent: Sep. 21, 2010

(54) TISSUE COLLECTION TRAY

(75) Inventors: Terry D. Hardin, Irvine, CA (US); Joseph L. Mark, Indianapolis, IN (US)

(73) Assignee: Suros Surgical Systems, Inc., Indianapolis, IN (US)

(*) Notice: Subject to any disclaimer, the term of this patent is extended or adjusted under 35 U.S.C. 154(b) by 263 days.

(21) Appl. No.: 12/033,967

(22) Filed: Feb. 20, 2008

(65) Prior Publication Data

US 2009/0050516 A1    Feb. 26, 2009

Related U.S. Application Data

(63) Continuation-in-part of application No. 29/283,627, filed on Aug. 20, 2007, now Pat. No. Des. 601,247.

(51) Int. Cl.
  *B65D 6/04* (2006.01)
  *A61B 17/02* (2006.01)
  *A61B 10/02* (2006.01)

(52) U.S. Cl. .................. 206/561; 206/438; 206/564; 206/569; 600/562; 600/567

(58) Field of Classification Search ......... 206/363–364, 206/370, 438–439, 557–565, 570–572; 128/845–846; 600/562–567; 604/317, 319, 356–357, 385.01, 604/385.06, 385.101
See application file for complete search history.

(56) References Cited

U.S. PATENT DOCUMENTS

| 636,735 | A |  | 11/1899 | Davenport |  |
|---|---|---|---|---|---|
| 3,987,895 | A |  | 10/1976 | Jamshidi |  |
| 4,655,494 | A |  | 4/1987 | Eads et al. |  |
| 4,728,521 | A | * | 3/1988 | Mitchell | 206/561 |
| D343,687 | S |  | 1/1994 | Houghton et al. |  |
| D346,655 | S |  | 5/1994 | Harris |  |
| 5,339,955 | A | * | 8/1994 | Horan et al. | 206/370 |
| 5,379,895 | A | * | 1/1995 | Foslien | 206/363 |
| 5,449,071 | A |  | 9/1995 | Levy |  |
| 5,779,053 | A | * | 7/1998 | Partika et al. | 206/570 |
| 5,944,014 | A | * | 8/1999 | Webb | 128/845 |
| 6,280,398 | B1 |  | 8/2001 | Ritchart et al. |  |
| D450,130 | S |  | 11/2001 | Goldstein |  |
| 6,540,694 | B1 |  | 4/2003 | Van Bladel et al. |  |
| 6,551,255 | B2 |  | 4/2003 | Van Bladel et al. |  |
| 6,719,691 | B2 |  | 4/2004 | Kritzman et al. |  |
| 6,976,968 | B2 |  | 12/2005 | Ritchart et al. |  |
| 6,984,213 | B2 |  | 1/2006 | Horner et al. |  |

(Continued)

OTHER PUBLICATIONS

Non-Final Office Action for U.S. Appl. No. 29/283,627 dated Aug. 15, 2008.

(Continued)

*Primary Examiner*—Bryon P Gehman
(74) *Attorney, Agent, or Firm*—Rader, Fishman & Grauer, PLLC

(57) ABSTRACT

A tissue collection tray is described for use with a biopsy device. The tissue collection tray includes a well portion, a body portion and a divider. The well portion is defined by first and second ends, a bottom and at least two walls. The body portion includes a recess formed therein. The divider includes a groove formed therein. The divider is positioned between the recess and the well portion.

23 Claims, 11 Drawing Sheets

U.S. PATENT DOCUMENTS

| | | | |
|---|---|---|---|
| 7,100,768 B2 * | 9/2006 | Grimard et al. | 206/438 |
| 7,278,987 B2 * | 10/2007 | Solazzo | 604/356 |
| D557,814 S | 12/2007 | Glenn et al. | |
| 2004/0116828 A1 * | 6/2004 | White, Jr. | 206/438 |
| 2006/0224083 A1 | 10/2006 | Clifford et al. | |
| 2007/0032740 A1 | 2/2007 | Quick et al. | |
| 2007/0149893 A1 | 6/2007 | Heske et al. | |
| 2007/0191731 A1 * | 8/2007 | Kaye et al. | 600/562 |
| 2007/0203513 A1 | 8/2007 | Vetter et al. | |
| 2008/0058672 A1 | 3/2008 | Shabaz et al. | |

OTHER PUBLICATIONS

Response to Non-Final Office Action for U.S. Appl. No. 29/283,627 dated Nov. 17, 2008.
Final Office Action for U.S. Appl. No. 29/283,627 dated Feb. 3, 2009.
Response to Final Office Action for U.S. Appl. No. 29/283,627 dated Apr. 3, 2009.
Notice of Allowance for U.S. Appl. No. 29/283,627 dated May 20, 2009.

* cited by examiner

TISSUE COLLECTION TRAY

RELATED APPLICATIONS

The present application is a continuation-in-part application of U.S. patent application Ser. No. 29/283,627, filed Aug. 20, 2007, entitled "Tissue Collection Tray," now U.S. Design Pat. D. 601,247 the contents of which are incorporated herein by reference in its entirety.

FIELD

The present disclosure relates to devices used in tissue extraction and more particularly, a tissue extraction device collection tray for containing tissue previously extracted using a core needle biopsy device.

BACKGROUND

Biopsy instruments are commonly known and used to obtain tissue samples to test for malignancy or other abnormalities and diseases. The biopsy instruments vary widely depending on the purported uses, including the target location of the biopsy as well as the size and type of tissue sample desired. The methods of extraction also vary based on such similar factors. Once the tissue has been extracted, it is necessary to carefully handle the sample and prepare it for microscopic examination or transfer and storage for future uses. Various receptacles exist which function to collect the tissue sample after extraction. It is desirable to have a collection tray or receptacle that is stable and easy to use during the critical and delicate tissue extraction process.

Core biopsy devices require an operator to carefully handle the biopsy device to avoid the possibility of coming in contact with a large needle used for removing a tissue sample from selected areas of the body such as breast or lung tissue. The tissue sample must be removed and preserved during handling and prior to microscopic examination. This process places the operator within close proximity of the needle enabling an opportunity for the operator to come in contact with the needle or the tissue sample and related fluids. There is also opportunity for the tissue sample to become contaminated by such contact.

Tissue collection trays are used to transport and preserve the biopsy specimen after being removed from the needle core of the biopsy device. A tissue collection tray permits the operator to control the collection of blood and other body fluids by stabilizing the biopsy needle through a groove in the tissue collection tray.

Tissue trays come in varied forms. One such example of a prior art tissue collection tray is shown in FIG. 1. The tissue collection tray of FIG. 1 includes multiple slots that that open into a shallow pan defined by a plurality of side walls and bottom surface. The shallow pan is designed so as to be capable of holding multiple samples. However, because the samples are deposited into the shallow pan there is no easy way of extracting the samples. Indeed, the individual samples are generally retrieved from the tray with another utensil or the tray is flipped over onto an observation medium, possibly damaging the sample or creating a biohazard risk for the operator.

Another pressing concern for medical professionals is to avoid the possibility of getting stuck with the needle. The prior art collection tray designs do not provide the medical professional with any protection from the possibility of such a biohazard risk.

What is needed, therefore, is a tissue collection tray that can contain a biopsy sample while eliminating possible contamination, as well as providing protection from possible needle probe sticks to the medical professional.

SUMMARY

A tissue collection tray is described for use with a biopsy device. The tissue collection tray includes a well portion, a body portion and a divider. The well portion is defined by first and second ends, a bottom and at least two walls. The body portion includes a recess formed therein. The divider includes a groove formed therein. The divider is positioned between the recess and the well portion.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION OF THE DRAWINGS

Figure 1:
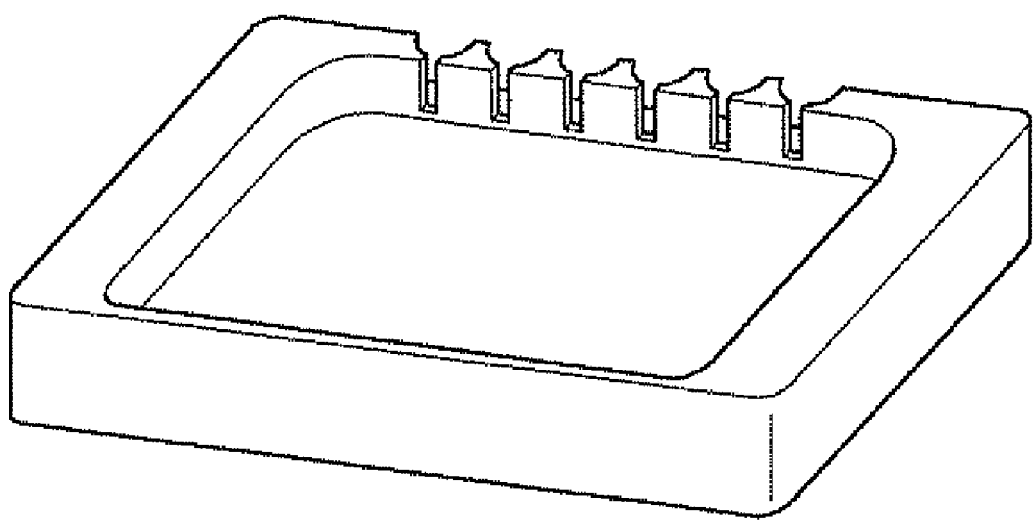
FIG. 1 is a perspective view of a prior art holding tray.

Referring to FIGS. 2-7, a first exemplary embodiment of a tissue collection tray 10 is provided. More specifically, FIGS.

2-7 illustrate alternative views of the tissue collection tray 10 that may be used to collect, store and transfer tissue samples extracted by a biopsy device, particularly a core needle biopsy device.

The tissue collection tray 10 includes a well portion 12 and a body portion 14. The well 12 and the body 14 portions of the tissue collection tray 10 may be formed as a unitary member. Alternatively, it is also contemplated that both the well 12 and the body 14 portions may be formed separately and then joined together to form the tissue collection tray 10 by a suitable method of attachment, including but not limited to gluing, fastening, or welding. Further, the tissue collection tray 10 (including both the well 12 and the body 14 portions) may be made of any suitable material for collecting, storing and preserving, and transferring tissue samples, including but not limited to flexible materials, non-permeable materials, glass, plastic and plastic variants, stainless steel, other suitable metals and other suitable synthetics.

Figure 2:
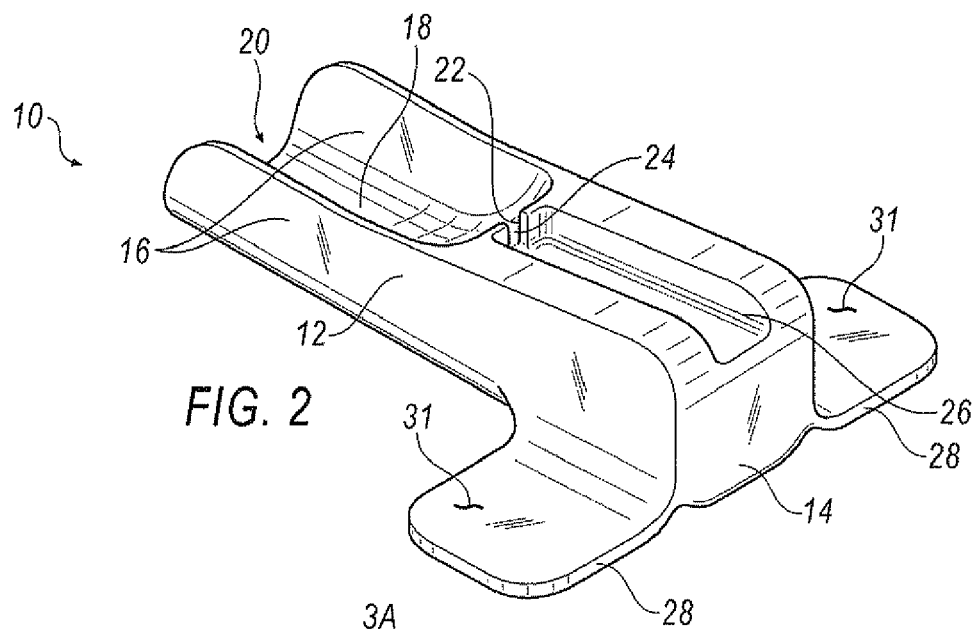
FIG. 2 is a rear perspective view of a tissue collection tray.
Figure 3:
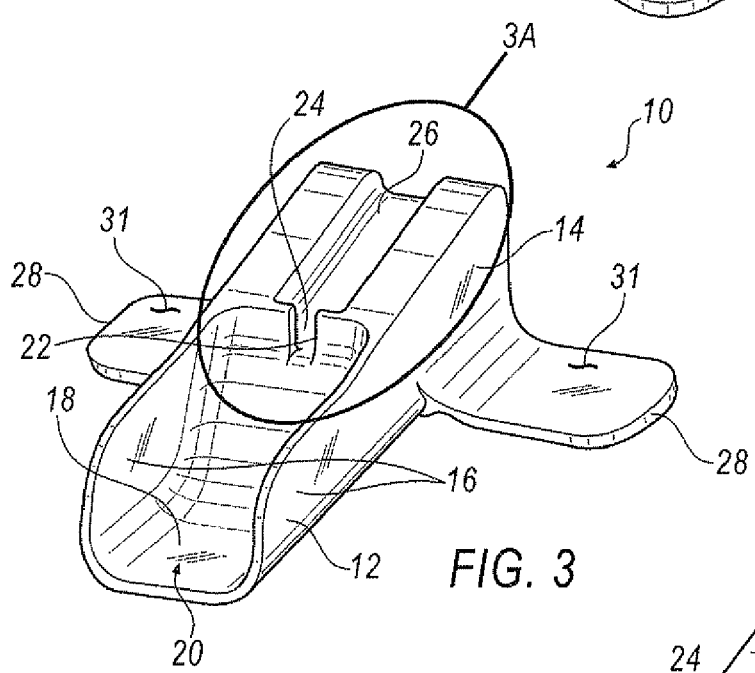
FIG. 3 is a front perspective view of the tissue collection tray of FIG. 2.

The well portion 12 is defined by at least two side walls 16, a bottom 18 and an outlet 20. The well portion 12 is defined by a first end 19 and a second end 21 (best seen in FIG. 6). The walls 16 may be integrally formed with the bottom 18 or may be formed separately and then attached to the bottom 18 by a suitable method of attachment. The shape of the well portion 12 is determined by the size, shape and arrangement of the walls 16 in connection with the bottom 18. In FIGS. 2-3, the well portion 12 is defined by two opposing substantially parallel walls 16 integrally formed with the bottom 18. It is contemplated that there may be more than two walls 16 that are in contact with the bottom 18 of well portion 12 to form multiple chambers (not shown). It is further contemplated that the size and shape of the well portion 12 may be varied depending on the purported use of the well portion 12, including collecting, sorting or storing several different tissue samples from one tissue extraction or a series of extractions.

Figure 5:
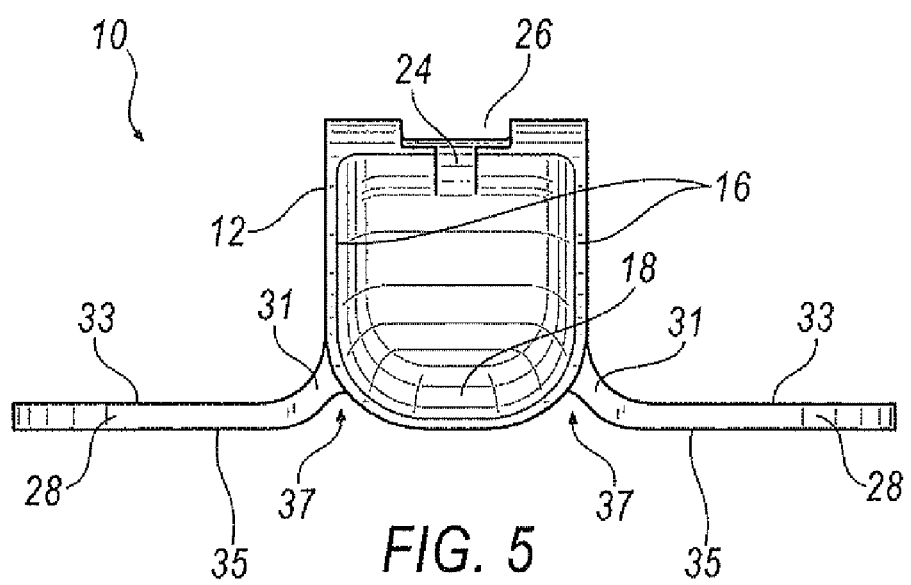
FIG. 5 is a front elevational view of the tissue collection tray of FIG. 2.

Referring to FIG. 5, the walls 16 are illustrated to be in continuous formation with the bottom 18 to form the well portion 12. The height of the walls 16 from the bottom 18 defines the depth of the well portion 12. It is contemplated that the walls 16 of well portion 12 may vary in thickness and height. It is further contemplated that walls 16 may form varying degrees of angles with bottom 18 to widen or narrow the well portion 12.

The bottom 18 of the well portion 12 may have an inclined surface that ends between the outlet 20 (located at the first end 19 of the well portion 12) and the second end 21. To be explained in further detail below, the inclined surface of bottom 18 may assist in the migration of the tissue sample towards the outlet 18 for easy transfer of a tissue sample to a storage container or to allow for multiple samples to be collected from one biopsy extraction. However, it is not necessary that the bottom 18 of the well portion 12 have an inclined surface.

The two walls 16 and bottom 18 open up to the outlet 20 at the first end of the well portion 12, as depicted. However, it is contemplated that outlet 20 may be located at any location around the well portion 12 that is suitable for the collection and transfer of the extracted tissue sample. FIGS. 2-3 and 5-6 depict the outlet 20 as having a relatively broad opening. However, it is contemplated that the outlet 20 of the well portion 12 may also be narrower or broader than depicted to accommodate the size and quantity of the tissue sample being collected. It is further contemplated that the outlet 20 may not be open as depicted, but rather may be partially or substantially blocked by a small barrier 32, shown in phantom in FIG. 11. Use of a barrier 32 may prevent undesirable fluids from spilling out of well portion 12, while not substantially impeding extraction of the tissue samples.

As depicted, the walls 16 and the bottom 18 are connected at the rear of the well portion 12 to form a divider 22. The divider 22 has a groove 24 formed therein that permits communicates between the well portion 12 and a recess 26 formed in the body portion 14. The divider 22 may be integrally formed with just the well 12 or just the body 14 and then attached to the other. Alternatively, the divider 22 may be continuous between the well 12 and the body 14.

Figure 4:
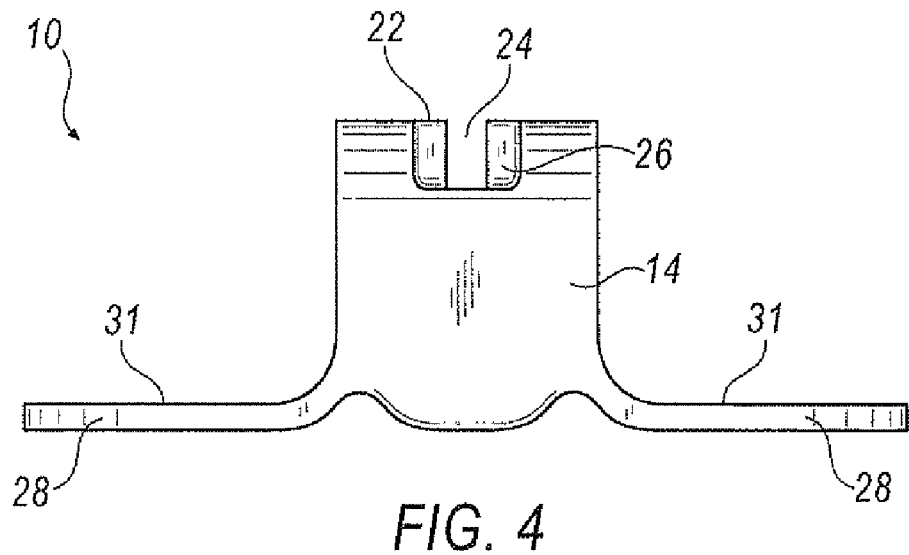
FIG. 4 is a rear elevational view of the tissue collection tray of FIG. 2.
Figure 11:
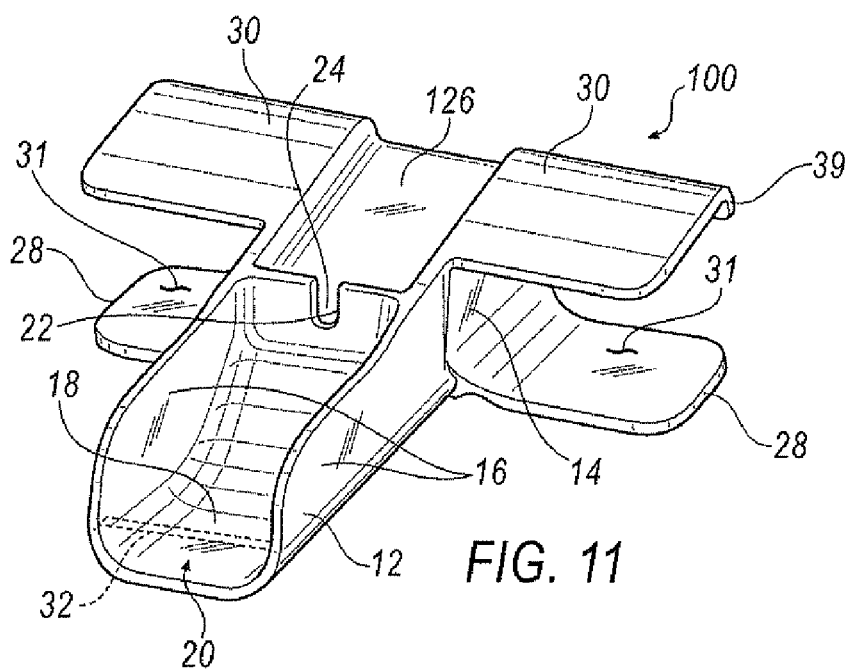
FIG. 11 is a front perspective view of the tissue collection tray of FIG. 10.

The groove 24 is depicted as a small and narrow opening in the divider 22. The shape of the groove 24 may alternatively be angular as depicted in FIG. 4, or rounded as depicted in FIG. 11. In general, varying widths and shapes of the groove 24 are contemplated. The groove 24 may function to guide and support a needle or other portion of a biopsy device during the extraction of tissue from the needle core. The groove 24 may further function to separate and remove the tissue sample from the needle after extraction without the need for operator contact with the sample, as will be explained in further detail below. Indeed, the groove 24 may make it unnecessary for the operator to use an additional tool to loosen and remove the tissue sample from the needle of the biopsy device, to be explained in further detail below.

In one embodiment, the recess 26 extends substantially the length of the body portion 14. However, it is not necessary for the recess 26 to extend the entire length of the body 14 and varying lengths of the recess 26 are contemplated. The recess 26 may be rounded, angular or have another shape that is suitable to receive a portion of a biopsy device. It is contemplated that the width and depth of recess 26 may also vary to accommodate the size of the desired biopsy device. Indeed, the recess 26 may function to receive, support and stabilize a biopsy device while retrieving a tissue sample from the needle of the biopsy device.

Figure 6:
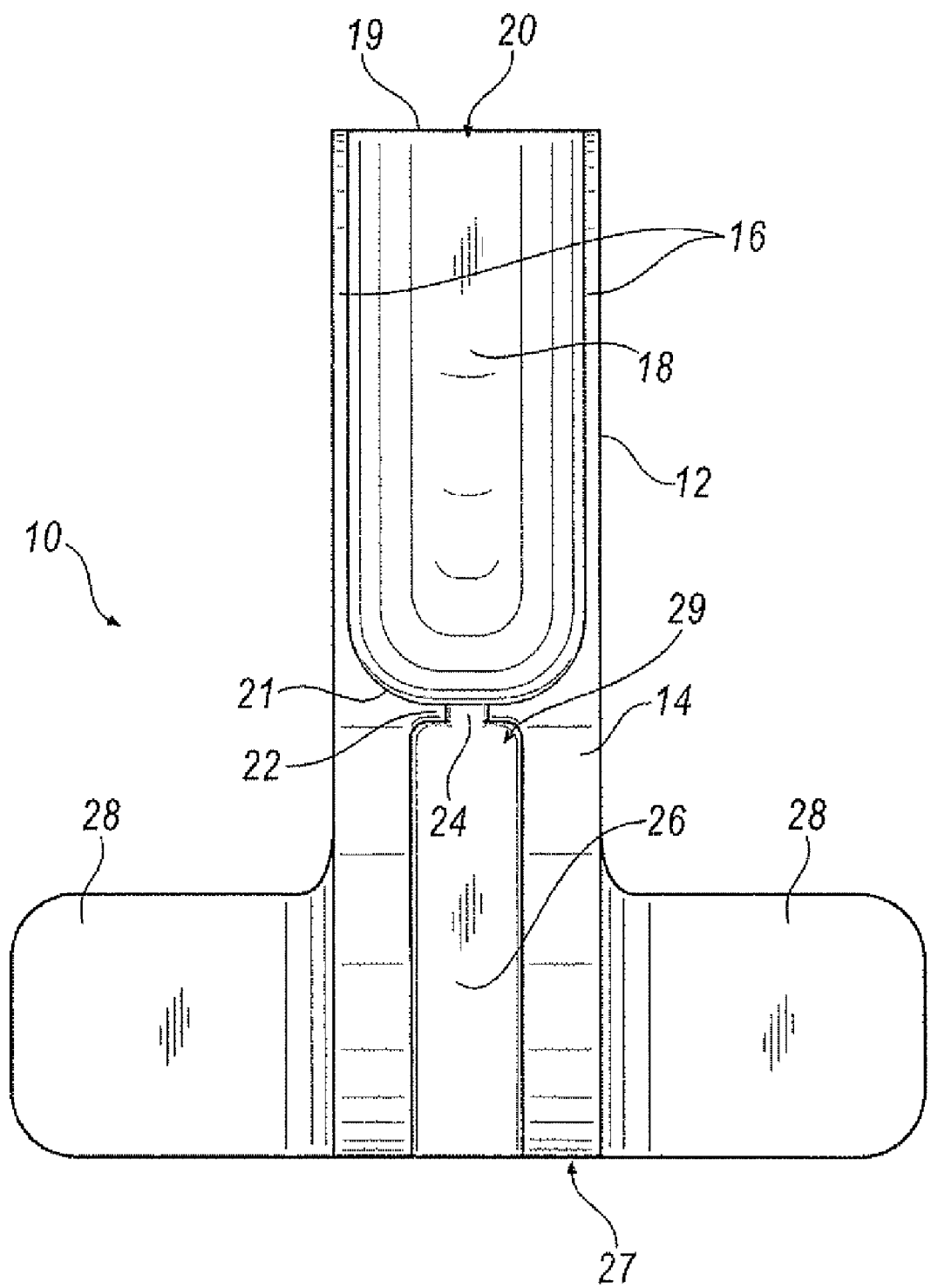
FIG. 6 is a top plan view of the tissue collection tray of FIG. 2.
Figure 7:
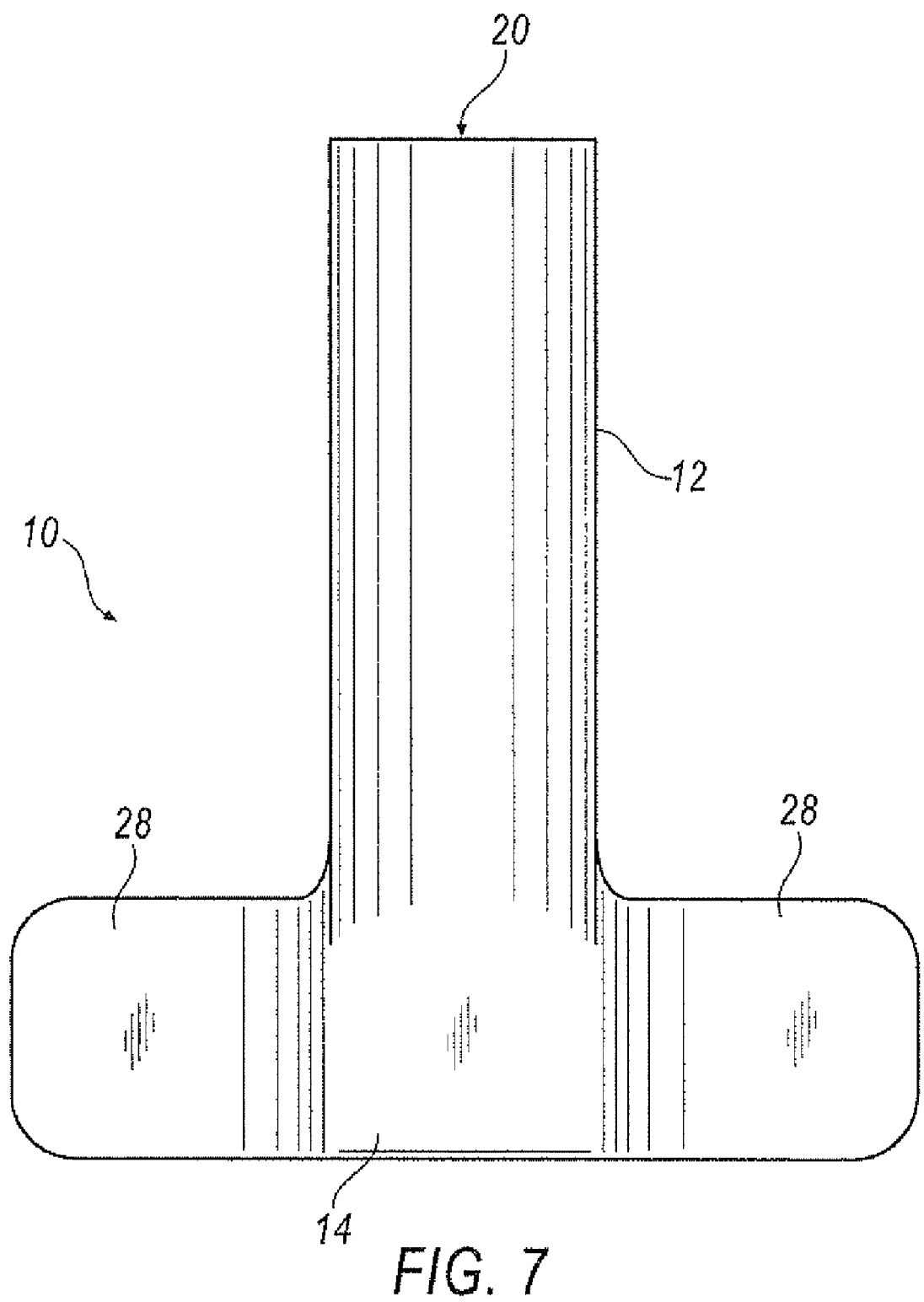
FIG. 7 is a bottom plan view of the tissue collection tray of FIG. 2.

The body portion 14 is defined by a first end 27 and a second end 29 (as best seen in FIG. 6). In on embodiment, the body portion 14 may further include at least one anchor 28 extending therefrom. Indeed in the embodiment shown in FIGS. 2-7, the tissue collection tray 10 includes a pair of opposing anchors 28 that extend outwardly from opposing side surfaces of body portion 14. In one embodiment, the anchors are configured so has to have a generally planar section such that the anchors 28 will rest on a generally flat surface, like a table. While body portion 14 is depicted as having two anchors 28, it is contemplated that the body 14 may have one anchor, two anchors, or more than two anchors. Further, the anchors 28 may be integrally formed with the body portion 14 or may be formed separately and attached by any suitable method. The anchors 28 are suitably configured to allow an operator to press against the anchor 28 with the operator's hand or fingers in order to stabilize and steady the tissue collection tray 10 during the collection process. The length and width of the anchors 28 may be proportionally varied depending on the size of the tissue collection tray 10 and the number of anchors present on the tissue collection tray 10. For example, if there is only one anchor present, the anchor 28 may be configured to extend away from the body 14 so as to offer increased support and stabilization of the tissue collection tray 10 during the tissue collection process.

FIGS. 4 and 5 illustrate the anchors 28 connected to side surfaces of the body portion 14 via a downwardly extending connecting member 31 to form a notched or curved feature 37. However, it is also contemplated that the anchors 28 may be directly connected to a bottom surface of the body portion 14, as shown in, for example FIGS. 8 and 9. Further, while the anchors 28 have been illustrated to be connected t to the body portion 14, it is also contemplated that the anchors may alternatively be connected to the well portion 12, or that the anchors 28 are configured with a width that extends between at least a section of the well portion 12 and the body portion 14.

The anchors 28 may also be formed with ridges or other frictional material on a top surface 33 thereof to provide a frictional contact surface for gripping the anchor 28. Similarly, a bottom surface 35 of the anchors may include a frictional contact surface to provide a gripping a surface for the tissue collection tray 10 when positioned on a table, for example.

Figure 3A:
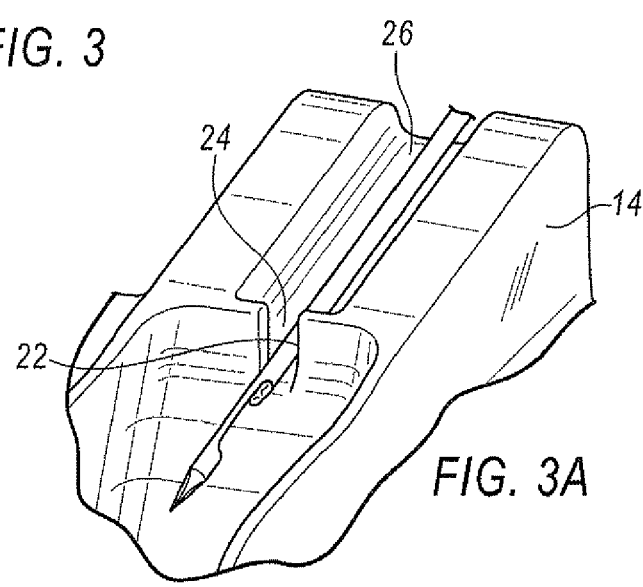
FIG. 3A is an enlarged view of area A taken from FIG. 3, illustrating a portion of a biopsy device engaged with a portion of the tissue collection tray.

In one example of use, referring to FIG. 3A, upon extracting a tissue sample for a patient using a needle core biopsy device or related biopsy device BD, an operator presses a hand or fingers against the anchor 28 to stabilize the tissue collection tray 10. The operator then rests a portion of the biopsy device BD in the recess 26 aligning the device in such a way that a portion of a needle of the biopsy device BD is received in the groove 24 of divider 22, with a tissue receiving opening positioned over the well portion 12 side of the divider 22. Once positioned, the operator then pulls back on the biopsy device BD, thereby moving the needle back through the groove 24 towards the body portion 14 of the tissue collection tray 10. The edges of the divider 22 that form groove 24 will assist in dislodging tissue samples from the biopsy needle for collection in the well portion 12. In one embodiment, at least the divider 22 is formed of a somewhat flexible material, to permit gentle dislodgement of the tissue sample. Additional tissue samples may be collected in the well 12 at this time as well.

When sample collection is completed, the operator transfers the tissue samples from well portion 12 by lifting and tipping the tissue collection tray 10 towards a collection container or jar containing formalin, or other suitable material used in preparation for a pathological examination. The tissue samples may migrate along the sloped bottom 18 of the well portion 12 and pass through the outlet 20 to be received by the collection jar. Throughout this process the operator has minimal exposure and contact with the tissue sample and the needle of the biopsy device.

Figure 8:
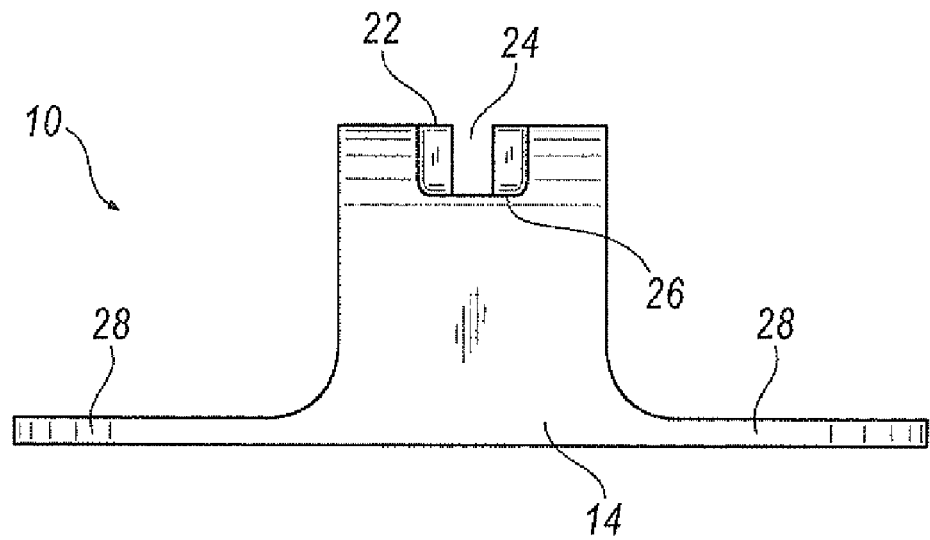
FIG. 8 is a rear elevational view of a second embodiment of a tissue collection tray.
Figure 9:
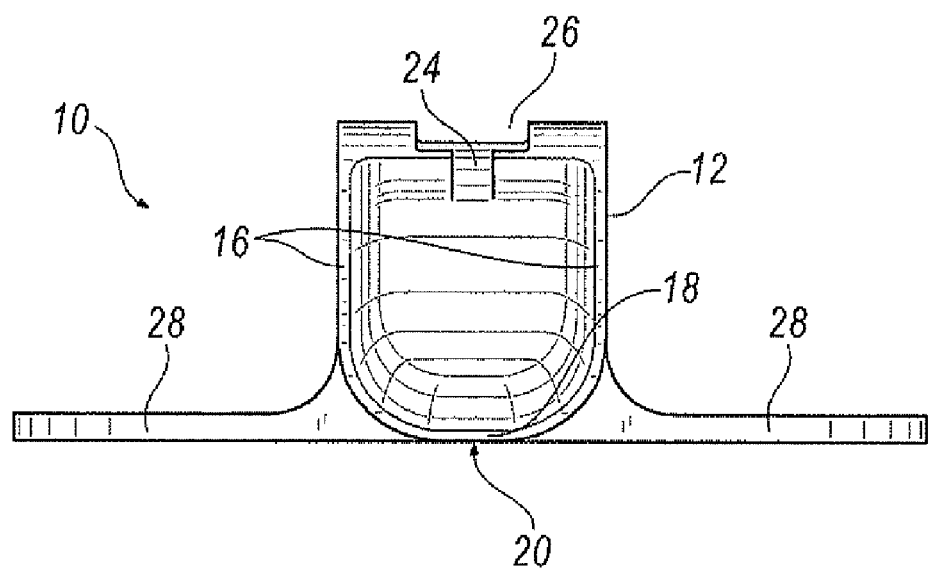
FIG. 9 is a front elevational view of the tissue collection tray of FIG. 8.
Figure 10:
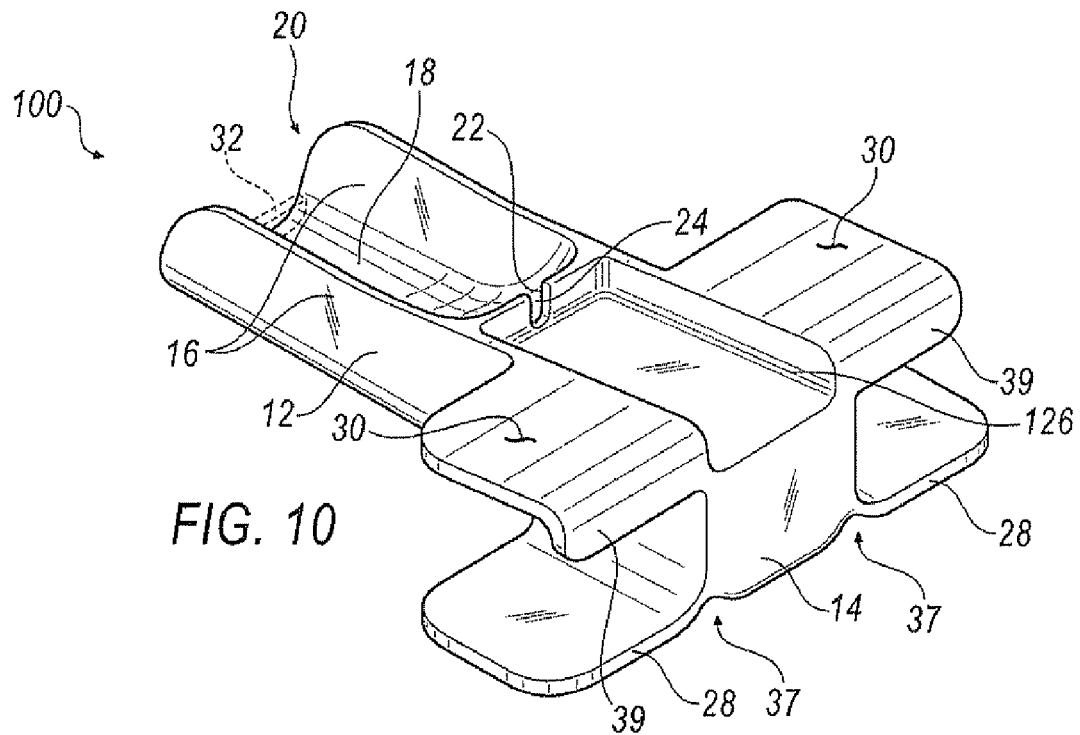
FIG. 10 is a rear perspective view of a third embodiment of a tissue collection tray.

FIGS. 8-9 depict an alternative embodiment of a tissue collection tray 10. The tissue collection tray 10 is configured such that it will rest on a substantially flat surface. For example, at least a portion of the bottom surface of the tissue collection tray 10 is depicted as having a flat or substantially flat configuration that rests on a flat or substantially surface. Alternatively, the tissue collection tray 10 may have a curved or notched configuration, as shown in FIGS. 5-6.

Groove 24 is depicted as being defined by generally squared corners and edges. However, it is also contemplated that groove 24 may be curved or rounded. The groove 24 may function to guide and support a needle or other portion of a biopsy device during the extraction of tissue from the device. The groove 24 may further function to separate and remove the tissue sample from the needle after extraction without the need for operator contact with the sample. For example, the needle of the biopsy device BD may be pulled back through the groove 24 causing the tissue sample to push against the divider 22. The tissue sample is thereby loosened and dislodged from the needle as it is being pulled back through the groove 24. This feature may negate the need for an additional tool to loosen and dislodge the tissue sample from the needle of the biopsy device BD.

FIGS. 10-15 depict another embodiment of a tissue collection tray 100. For convenience, elements in common with the embodiments shown in FIGS. 1-9 will be given like numbers.

Figure 16:
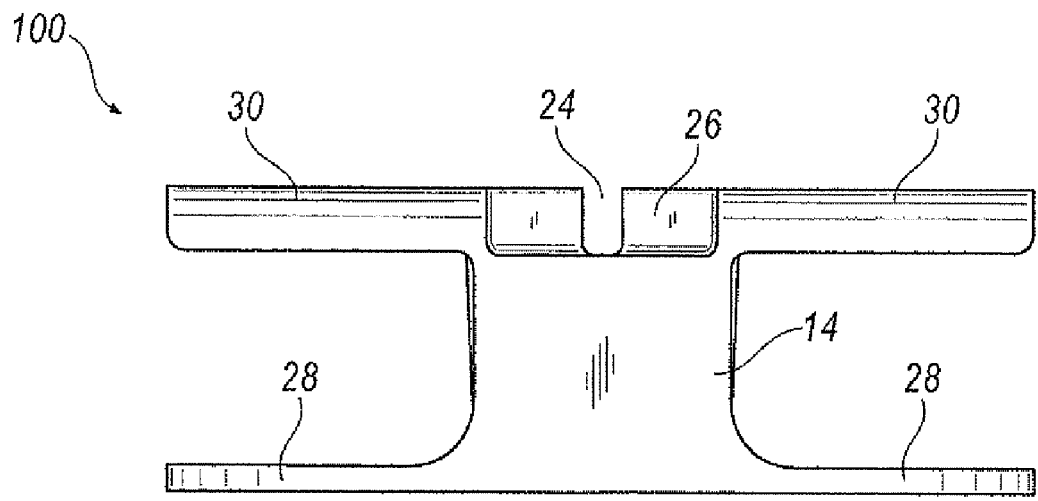
FIG. 16 is a rear elevational view of a fourth embodiment of a tissue collection tray.
Figure 17:
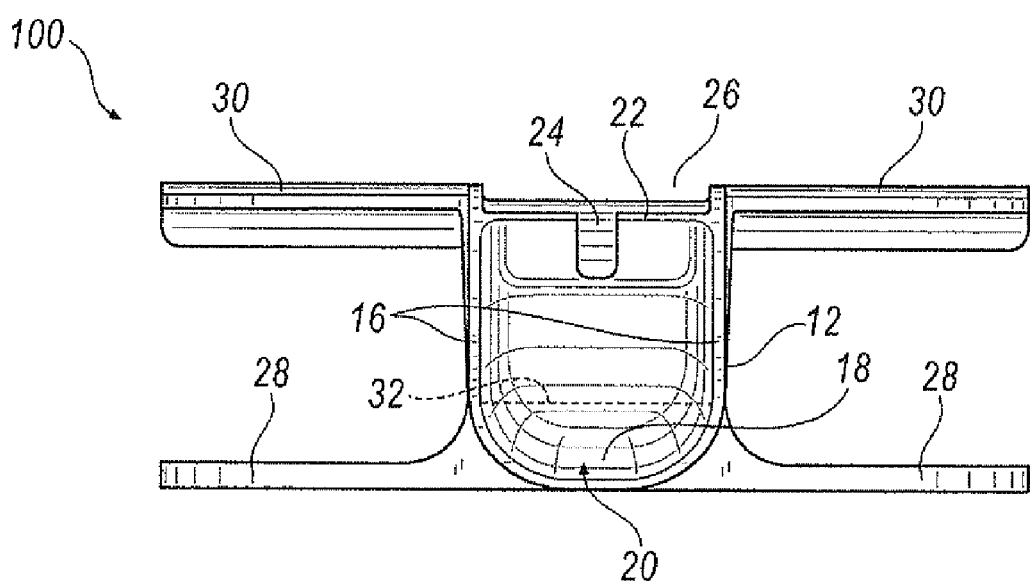
FIG. 17 is a front elevational view of the tissue collection tray of FIG. 16.

The tissue collection tray 100 is configured such that it will rest on a substantially flat surface. More specifically, the tissue collection tray 100 is depicted as having a curved or notched feature 37 defined by anchors 28 and connectors 31. The anchors 28 extend outwardly from the connectors 31 in a generally planar configuration so as to define a generally planar surface. Alternatively, the tissue collection tray 100 may be configured to be substantially planar so as to rests on a flat surface, as shown in FIGS. 16-17.

In addition to anchors 28, tissue collection tray 100 further includes at least one wing 30. In one embodiment, there are two opposing wings 30 provided. Wings 30 are attached to a portion of body portion 14 and extend outwardly and away from the body portion 14. In one embodiment, the wings 30 are configured to be parallel or substantially parallel to the anchors 28, leaving a gap therebetween. While body portion 14 is depicted as having two wings 30, it is contemplated that the body 14 may have one wing, two wings, or more than two wings. The wings 30 may be integrally formed with the body 14 or may be formed separately and attached by any suitable method. The wings 30 function to act as a shield for an operator's hand and/or fingers to protect them from coming into contact with the tissue samples, blood and related fluids, or the needle itself. Indeed, while the operator is pressing against the anchors 28 with the operator's hand or fingers, the wings 30 may protect the operator's hand and fingers from exposure to various fluids, the tissue samples or the needle. The length and width of the wings 30 may be proportionally varied depending on the size of the tissue collection tray 100. Additionally, the wings 30 may be configured to be planar, substantially planar or partially curved. Further a distal end of the wings 30 may be provided with a downwardly extending wall 39 to further protect a user's hands or fingers.

Similar to the embodiments shown in FIGS. 1-9, The tissue collection tray 100 includes a recess 126 disposed in the body portion 14. However, the recess 126 is configured to have a wide area to receive and support a portion of the tissue biopsy device BD. Recess 26 communicates with the groove 24 disposed in divider 22. Here, groove 24 is depicted as having a curved shape. The groove 24 may function to guide and support a needle portion of a biopsy device during the extraction of tissue from the needle. The groove 24 may further function to separate and remove the tissue sample from the needle after extraction without the need for operator contact with the sample. For example, the groove 24 may make it unnecessary for the operator to use an additional tool to loosen and remove the tissue sample from the needle of the biopsy device.

At the first end of well portion 12, an optional barrier 32 may be situated against or near the bottom 18 and between the walls 16 to partially, substantially or completely block the outlet 20 of well 12. The barrier 32 may function to contain the tissue samples and related fluids. It is contemplated that the barrier 32 may be made of a solid material that will substantially contain the tissue sample and any related fluids. It is further contemplated that the barrier 32 may be made of a porous material capable of filtering out fluid or smaller pieces of tissue in order to retain the desired tissue sample without the fluid. In one embodiment, the barrier 32 may be configured with a hinge mechanism that would permit the barrier to be pivoted about the bottom 18 of the well portion to permit tissue samples to be poured out of well portion 12. Alternatively, barrier 32 may also be selectively removable from the well portion 12.

Figure 12:
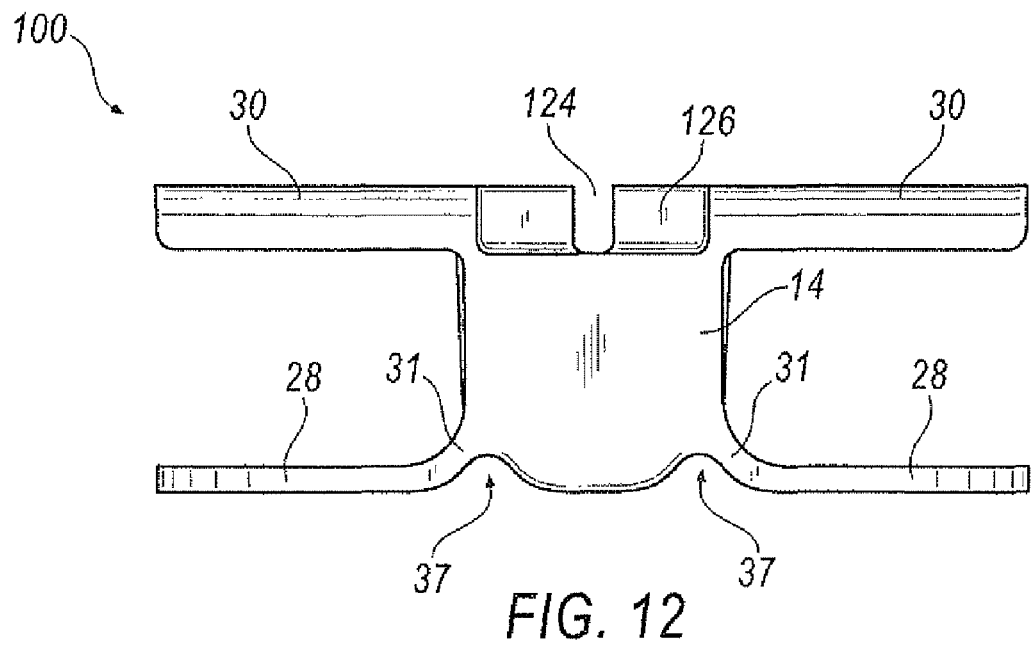
FIG. 12 is a rear elevational view of the tissue collection tray of FIG. 10.
Figure 13:
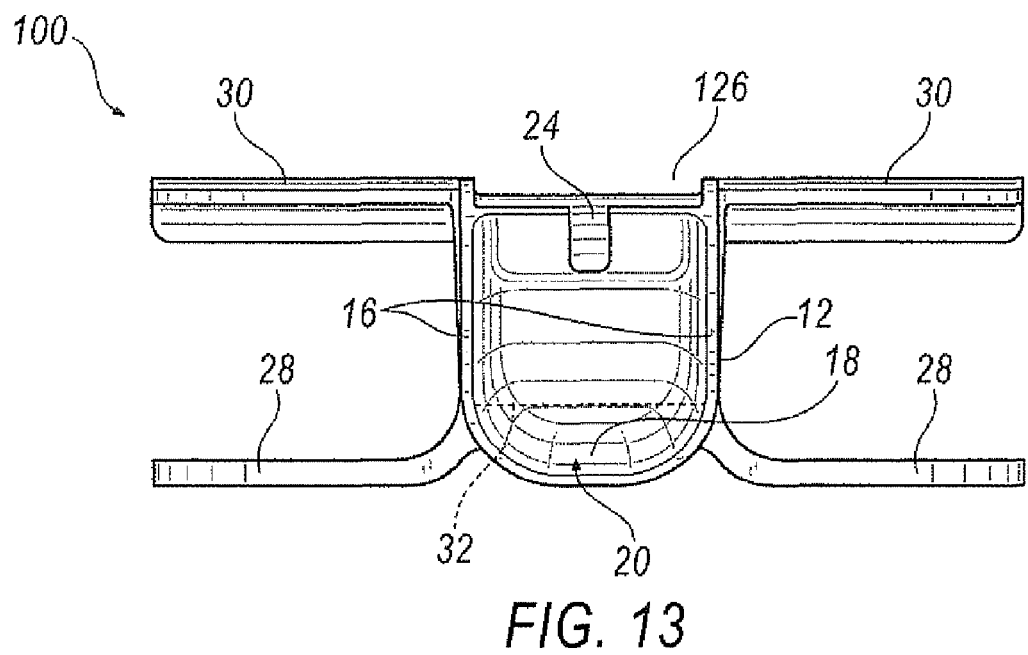
FIG. 13 is a front elevational view of the tissue collection tray of FIG. 10.
Figure 14:
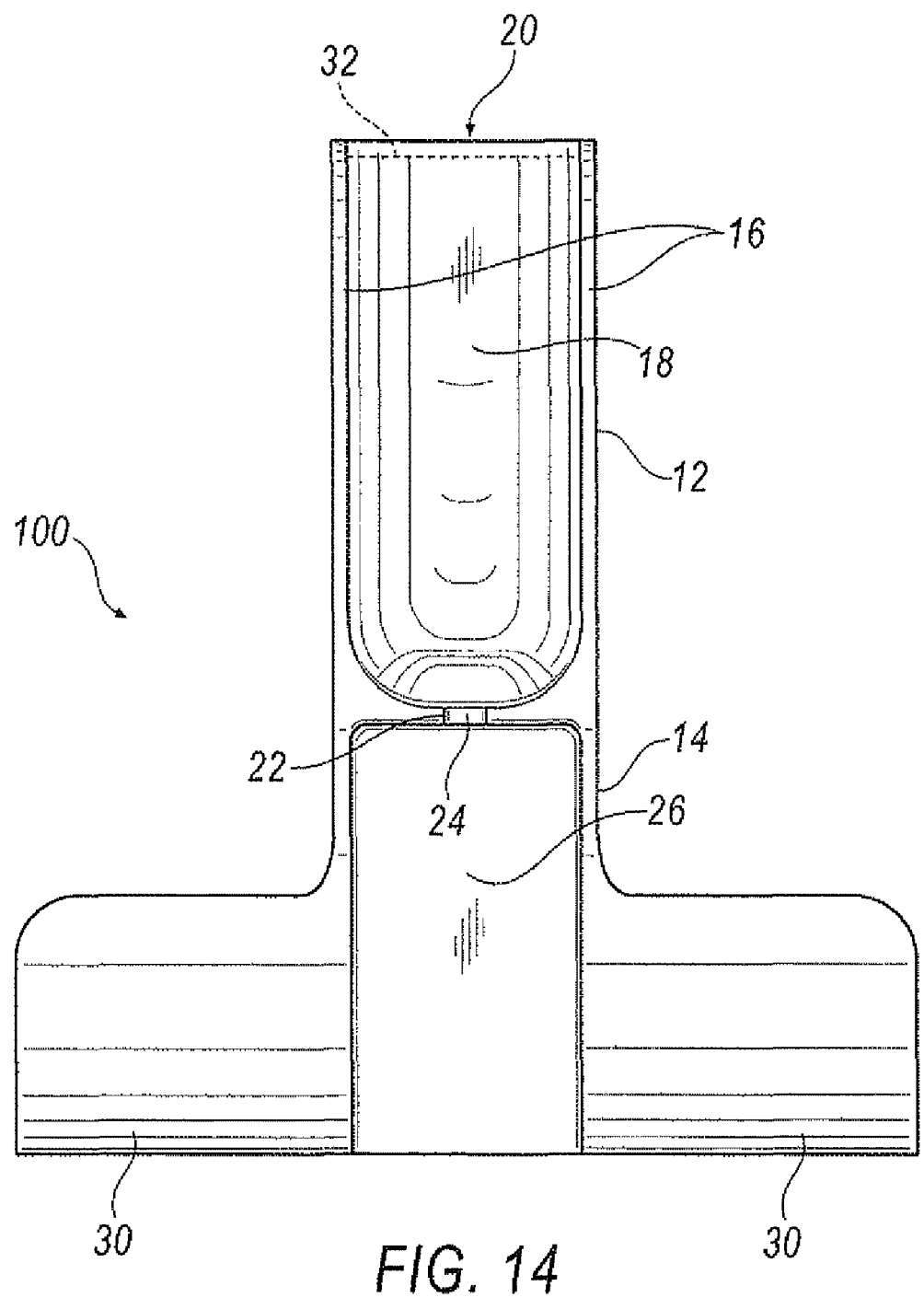
FIG. 14 is a top plan view of the tissue collection tray of FIG. 10.
Figure 15:
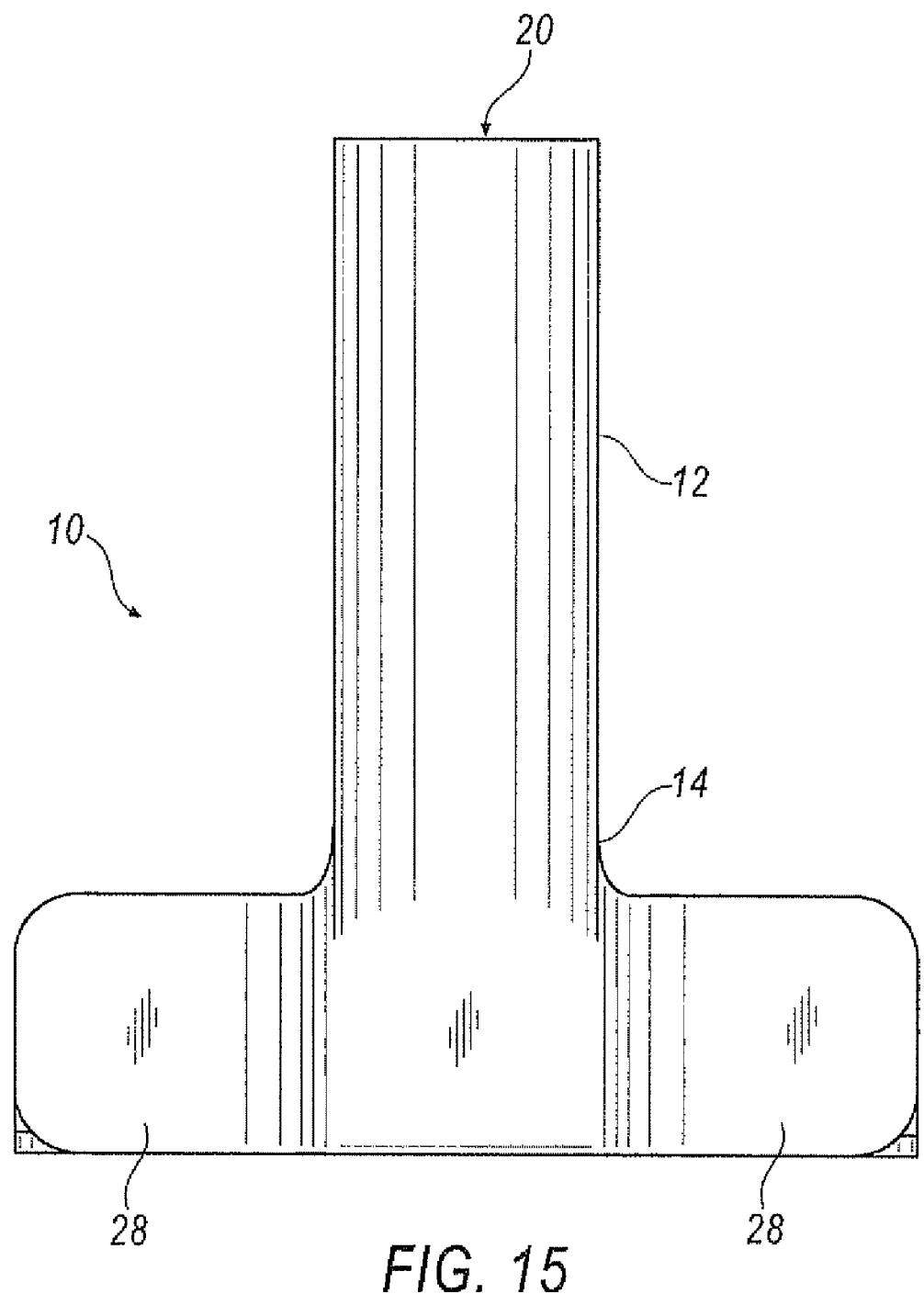
FIG. 15 is a bottom plan view of the tissue collection tray of FIG. 11.

FIGS. 16-17 depict a fourth embodiment of a tissue collection tray 100. In this embodiment the tissue collection tray 100 is configured such that it will rest on a substantially flat surface. More specifically, in this embodiment, the anchors 28 of the tissue collection tray 100 are configured as being substantially planar from the point it attaches to the body portion 14 to the end of their respective spans. Alternatively, the tissue collection tray 100 may have a curved or notched feature 37, as depicted in FIGS. 12-13.

Also in this embodiment, body portion 14 includes at least one wing 30 that extends away from the body portion 14. Indeed, in one embodiment, the wing 30 is parallel or substantially parallel to at least one anchor 28. The wing 30 may help to shield the operator from possible contact with the core biopsy needle or the tissue sample. Wing 30 may further assist in preventing contamination of the tissue sample from such contact.

The preceding description has been presented only to illustrate and describe exemplary embodiments of the methods and systems of the present disclosure. It is not intended to be exhaustive or to limit the disclosure to any precise form disclosed. It will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope. Therefore, it is intended that the disclosure not be limited to the particular embodiment disclosed as the best mode contemplated for carrying out this disclosure, but that the disclosure will include all embodiments falling within the scope of the claims. The disclosure may be practiced otherwise than is specifically explained and illustrated without departing from its spirit or scope. The scope of the disclosure is limited solely by the following claims.

What is claimed is:

1. A tissue collection tray comprising:
   a well portion defined by a first end and a second end, a bottom, and at least two walls, wherein the well portion inclines downwardly from the second end of the well portion to an outlet positioned at the first end of the well portion;
   a body portion adjacent the well portion having a recess formed therein, wherein the recess is defined by a first end and a second end, the first end of the recess being open; and
   a divider having a groove formed therein, wherein the divider is positioned between the recess and the well portion such that the divider is positioned at the second end of the recess.

2. The tissue collection tray of claim 1, further comprising at least one anchor extending outwardly from a portion of the tissue collection tray.

3. The tissue collection tray of claim 2, wherein the at least one anchor is positioned adjacent to a bottom portion of the tissue collection tray such that the at least one anchor extends outwardly from the body portion of the tissue collection tray.

4. The tissue collection tray of claim 2, wherein the at least one anchor is configured to have a substantially planar bottom surface.

5. The tissue collection tray of claim 2, wherein the tissue collection tray includes opposing anchors disposed on either side of the tissue collection tray.

6. The tissue collection tray of claim 2, wherein the at least one anchor is connected to a portion of the collection tray by an angled connector member.

7. The tissue collection tray of claim 2, wherein the at least one anchor is connected to the body portion of the tissue collection tray.

8. The tissue collection tray of claim 2, further comprising a wing extending outwardly from a portion of the tissue collection tray and disposed at least partially over an anchor and spaced away so at to create a gap between the anchor and the wing.

9. The tissue collection tray of claim 1, wherein the collection tray is configured as a unitary and integral structure.

10. The tissue collection tray of claim 1, wherein the divider is constructed of a flexible material.

11. The tissue collection tray of claim 1, further comprising a barrier disposed at the first end of the well portion, wherein the barrier is configured as an upwardly extending wall member.

12. The tissue collection tray of claim 11, wherein at least a portion of the barrier may be selectively detached from the well portion of the tissue collection tray.

13. The tissue collection tray of claim 11, wherein the barrier is constructed of a porous material that permits fluid to pass through.

14. The tissue collection tray of claim 1, wherein the recess is defined by a first depth and wherein the well portion defines a second depth, wherein the first depth is less than the second depth.

15. The tissue collection tray of claim 1, wherein the recess is inclines downwardly from the first end of the recess to the second end of the recess.

16. The tissue collection tray of claim 15, wherein the degree of incline of the recess is less than the degree of incline of the well portion.

17. The tissue collection tray of claim 1, wherein the divider is defined by a top surface that is generally flush with a top surface of the body portion.

18. A tissue collection tray comprising:
    a well portion defined by a first end and a second end, a bottom, and at least two walls; wherein the well portion is inclined toward an outlet positioned at the first end;
    a body portion adjacent the well portion having a recess formed therein, wherein the recess is defined by, the first end being open;
    a divider having a groove formed therein that is configured to receive a portion of a biopsy needle, wherein the divider is positioned between the recess and the well portion, thereby separating the well portion and the body portion; and
    at least one anchor extending outwardly from a portion of the tissue collection tray.

19. The tissue collection tray of claim 18, wherein the at least one anchor is configured to have a substantially planar bottom surface.

20. The tissue collection tray of claim 18, further comprising at least one wing extending outwardly from a portion of the tissue collection tray and disposed at least partially over the at least one anchor and spaced away so at to create a gap between the anchor and the wing.

21. The tissue collection tray of claim 20, wherein the tissue collection tray includes opposing anchors disposed on either side of the tissue collection tray and two opposing wings disposed on either side of the tissue collection tray.

22. The tissue collection tray of claim 18, further comprising a barrier disposed at the outlet of the well portion, wherein the barrier is configured as an upwardly extending wall member.

23. The tissue collection tray of claim 22, wherein at least a portion of the barrier may be selectively detached from the well portion of the tissue collection tray.

* * * * *

UNITED STATES PATENT AND TRADEMARK OFFICE
CERTIFICATE OF CORRECTION

PATENT NO.        : 7,798,331 B2                                            Page 1 of 1
APPLICATION NO.   : 12/033967
DATED             : September 21, 2010
INVENTOR(S)       : Terry D. Hardin et al.

It is certified that error appears in the above-identified patent and that said Letters Patent is hereby corrected as shown below:

Column 8, claim 8, line 4, please change [[at]] to --as--;

Column 8, claim 15, line 25, please delete the word "is";

Column 8, claim 20, line 53, please change [[at]] to --as--.

Signed and Sealed this

Ninth Day of November, 2010

David J. Kappos
*Director of the United States Patent and Trademark Office*